United States Patent
Kojima et al.

(10) Patent No.: US 12,121,380 B2
(45) Date of Patent: Oct. 22, 2024

(54) PCCT APPARATUS

(71) Applicant: FUJIFILM Healthcare Corporation, Kashiwa (JP)

(72) Inventors: Shinichi Kojima, Kashiwa (JP); Fumito Watanabe, Kashiwa (JP); Isao Takahashi, Kashiwa (JP); Kazuma Yokoi, Kashiwa (JP); Taiga Goto, Kashiwa (JP); Fuyuhiko Teramoto, Kashiwa (JP); Ryosuke Tsuchida, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 244 days.

(21) Appl. No.: 17/964,642

(22) Filed: Oct. 12, 2022

(65) Prior Publication Data
US 2023/0233164 A1    Jul. 27, 2023

(30) Foreign Application Priority Data

Jan. 25, 2022   (JP) .................................. 2022-009021

(51) Int. Cl.
*A61B 6/00* (2024.01)
*A61B 6/03* (2006.01)
*A61B 6/42* (2024.01)

(52) U.S. Cl.
CPC ............ *A61B 6/4241* (2013.01); *A61B 6/032* (2013.01); *A61B 6/5205* (2013.01); *A61B 6/5258* (2013.01)

(58) Field of Classification Search
CPC .. A61B 6/00; A61B 6/03; A61B 6/032; A61B 6/035; A61B 6/4241; A61B 6/482; A61B 6/5205; A61B 6/5258; A61B 6/582; A61B 6/583
See application file for complete search history.

(56) References Cited

U.S. PATENT DOCUMENTS 11,896,410 B2 *   2/2024   Kojima .................. A61B 6/583

FOREIGN PATENT DOCUMENTS

JP         2009-050413 A         3/2009

* cited by examiner

*Primary Examiner* — Jurie Yun
(74) *Attorney, Agent, or Firm* — Paul Teng

(57) ABSTRACT

There is provided a PCCT apparatus capable of correcting a band artifact of one material decomposition image and a band artifact of another material decomposition image. The PCCT apparatus obtains projection data divided into plural energy bins by irradiating a subject with X-rays, and includes: a first correction unit that corrects a band artifact of a first material decomposition image among plural material decomposition images created on the basis of the projection data, and calculates a first correction amount that is a correction amount for the band artifact; an energy calculation unit that calculates an average energy of X-rays that transmit the subject; and a second correction unit that corrects the band artifact of a second material decomposition image using a second correction amount that is a correction amount calculated on the basis of the first correction amount and the average energy.

6 Claims, 8 Drawing Sheets

FIG. 4

| | | | ACRYLIC | | | | |
|---|---|---|---|---|---|---|---|
| | | | 0mm | 50mm | 100mm | 150mm | 200mm |
| ALUMINUM | 0mm | bin1 | 2000 | 1748 | 1529 | 1337 | 1169 |
| | | bin2 | 3000 | 2706 | 2441 | 2202 | 1987 |
| | | bin3 | 2500 | 2280 | 2080 | 1897 | 1731 |
| | 2mm | bin1 | 1916 | 1675 | 1465 | 1281 | 1120 |
| | | bin2 | 2954 | 2665 | 2404 | 2169 | 1957 |
| | | bin3 | 2478 | 2261 | 2062 | 1881 | 1716 |
| | 4mm | bin1 | 1835 | 1605 | 1403 | 1227 | 1073 |
| | | bin2 | 2909 | 2624 | 2367 | 2136 | 1927 |
| | | bin3 | 2457 | 2241 | 2045 | 1865 | 1701 |
| | 6mm | bin1 | 1758 | 1538 | 1344 | 1176 | 1028 |
| | | bin2 | 2864 | 2584 | 2331 | 2103 | 1897 |
| | | bin3 | 2436 | 2222 | 2027 | 1849 | 1687 |
| | 8mm | bin1 | 1685 | 1473 | 1288 | 1126 | 985 |
| | | bin2 | 2820 | 2544 | 2295 | 2071 | 1868 |
| | | bin3 | 2415 | 2203 | 2010 | 1834 | 1673 |

521

PCCT APPARATUS

CLAIM OF PRIORITY

The present application claims priority from Japanese Patent Application No. 2022-009021 filed on Jan. 25, 2022, the content of which is hereby incorporated by reference into this application.

BACKGROUND OF THE INVENTION

The present invention relates to the correction of artifacts in material decomposition images that are created on the basis of projection data obtained and divided into a plurality of energy bins by a photon counting type detector or the like, and each of which discriminatively shows one of materials existing in a subject.

A PCCT (Photon Counting Computed Tomography) apparatus equipped with photon counting type detectors that are detectors adopting photon counting schemes is capable of providing a medical image that contains more information than a conventional CT apparatus. For example, the PCCT apparatus can provide energy bin images created using projection data divided into a plurality of energy bins, and material decomposition images each of which discriminatively shows one of a plurality of materials.

Meanwhile, in an X-ray CT image, artifacts due to beam hardening in sites having high X-ray absorption coefficients such as a bone tissue in a subject or a metal member for medical treatment, for example, dark bands that exists between sites having high X-ray absorption coefficients and have low CT values are sometimes generated. Artifacts due to beam hardening are corrected by, for example, a method disclosed in Japanese Unexamined Patent Application Publication No. 2009-50413.

SUMMARY OF THE INVENTION

However, in Japanese Unexamined Patent Application Publication No. 2009-50413, consideration is not given to a band artifact such as a dark band generated in a material decomposition image. When a dark band is generated in one material decomposition image, a bright band is generated in the other material decomposition image, so that it is insufficient to execute correction on only one band artifact.

Therefore, an object of the present invention is to provide a PCCT apparatus capable of correcting the band artifact of one material decomposition image and the band artifact of the other material decomposition image as well.

In order to achieve the abovementioned object, the present invention is a PCCT apparatus that obtains projection data divided into a plurality of energy bins by irradiating a subject with X-rays, and the PCCT apparatus includes: a first correction unit that corrects a band artifact of a first material decomposition image among a plurality of material decomposition images created on the basis of the projection data, and at the same time, calculates a first correction amount that is a correction amount for the band artifact; an energy calculation unit that calculates an average energy of X-rays that transmit the subject; and a second correction unit that corrects the band artifact of a second material decomposition image using a second correction amount that is a correction amount calculated on the basis of the first correction amount and the average energy.

According to the present invention, a PCCT apparatus capable of correcting the band artifact of one material decomposition image and the band artifact of the other material decomposition image as well can be provided.

BRIEF DESCRIPTION OF THE DRAWINGS

FIG. 4 is a diagram showing an example of a material decomposition map;

DETAILED DESCRIPTION OF THE PREFERRED EMBODIMENTS

Figure 1:
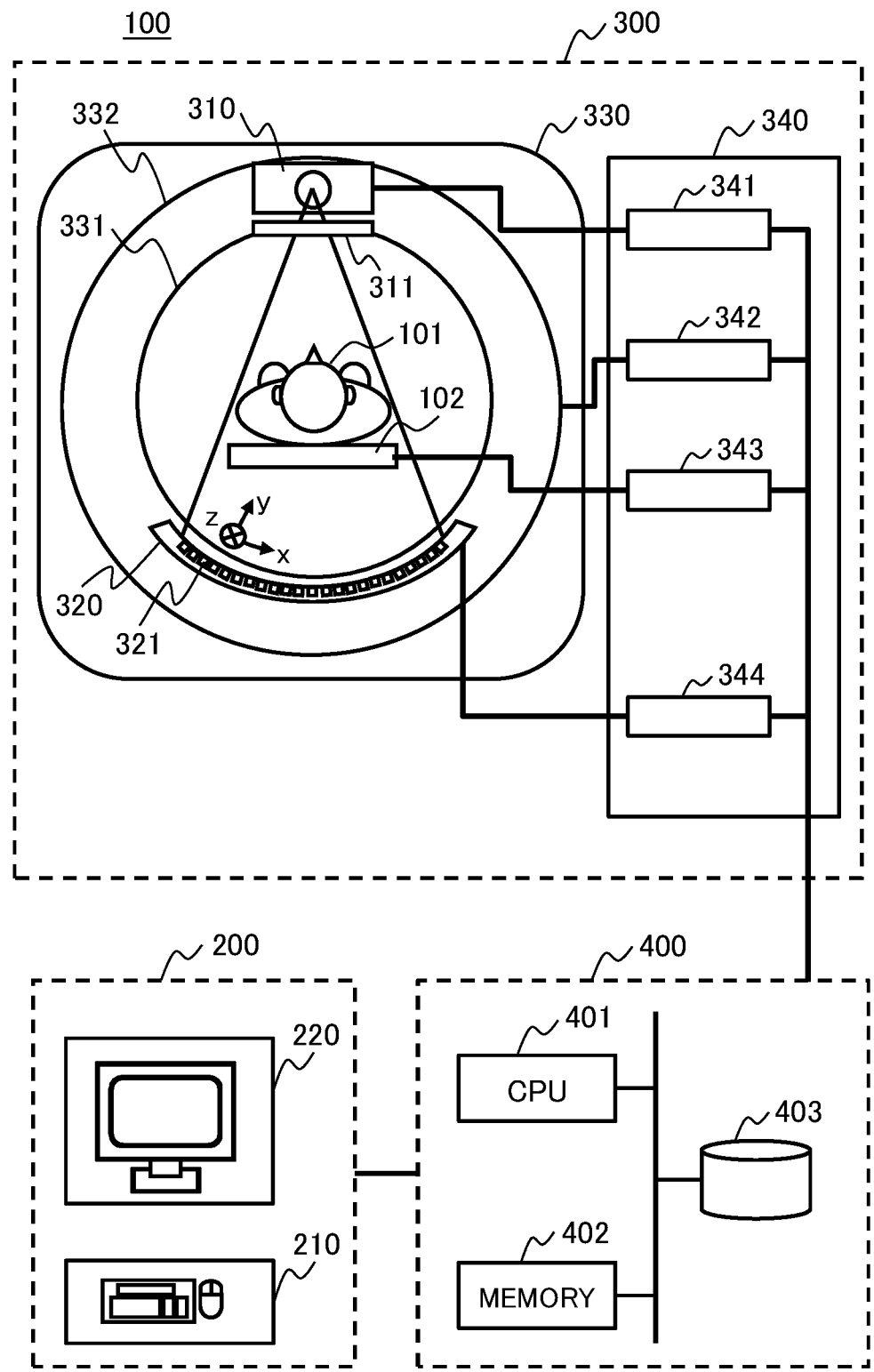
FIG. 1 is a diagram showing the overall configuration of a PCCT apparatus.

Hereinafter, an embodiment of a PCCT (Photon Counting Computed Tomography) apparatus according to the present invention will be described with reference to the accompanying drawings. Here, in the following descriptions and drawings, redundant explanations about components having the same functional configurations will be omitted by giving the same reference signs to the components.

First Embodiment

The overall configuration of a PCCT apparatus 100 will be described with reference to FIG. 1. The PCCT apparatus 100 includes: an input/output unit 200; a scanning unit 300; and an integral control unit 400.

The input/output unit 200 includes an input device 210 and a monitor 220. The input device 210 is a device used for an operator inputting scanning conditions and the like, and for example, a mouse or a keyboard. The monitor 220 is a display device for outputting inputted scanning conditions and the like, and if the monitor 220 has a touch panel function, the monitor 220 can also be used as the input device 210.

The scanning unit 300 includes: an X-ray source 310; an X-ray detection device 320; a gantry 330; a table 102; and a scanning control unit 340 in order to obtain projection data of a subject 101 at various projection angles. Here, the obtained projection data is divided into a plurality of energy bins.

The X-ray source 310 is a device for irradiating the subject 101 with X-rays. A collimator 311 is provided between the X-ray source 310 and the subject 101. The collimator 311 is a device for adjusting the lengths of X-rays emitted to the subject 101 in the z direction.

The X-ray detection device 320 is a device for detecting direct rays that are X-rays which transmits through the subject 101 without being scattered, and includes a plurality of detection elements 321. The detection elements 321, about 1000 of them, are disposed at locations equidistant from the X-ray generation point of the X-ray source 310, for example, at locations 1000 mm away. Each of the detection elements 321 is an element for detecting X-rays, and outputs an electric signal corresponding to the amount of X-rays incident on each detection element. The detection elements 321 are disposed on the xy plane, and each of the detection elements 321 has a size of, for example, 0.5 mm square. A detection element 321 may be an indirect type detection element including a combination of a scintillator element and a photodiode element, or may also be a semiconductor detection element typified by a CdTe detection element. In the indirect type detection element, the scintillator element emits fluorescence due to incident X-rays, and the fluorescence is converted into an electric signal by the photodiode element.

Figure 2:
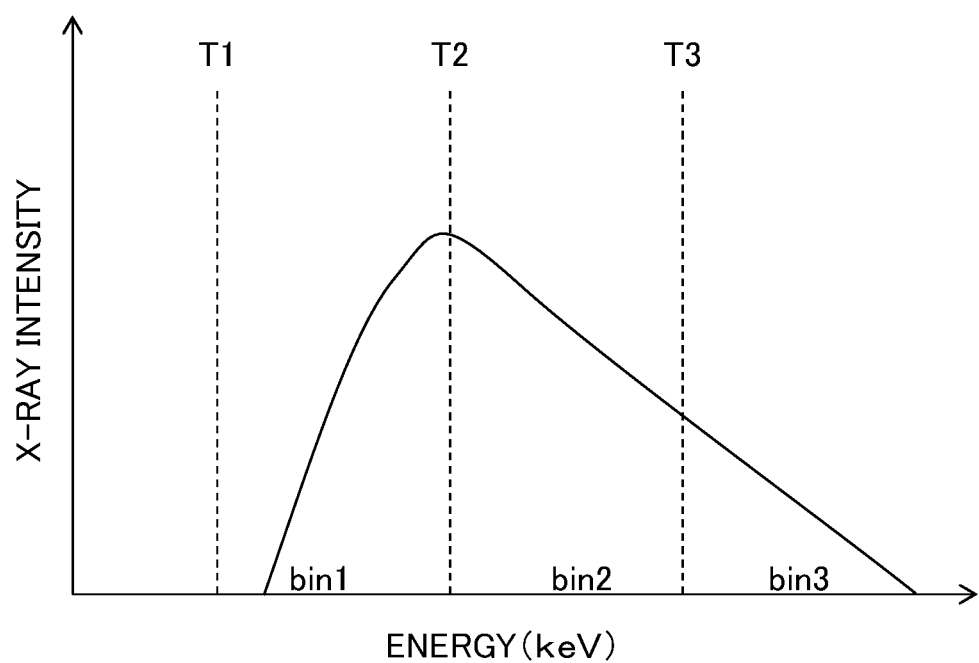
FIG. 2 is a diagram showing examples of X-rays divided into a plurality of energy bins.

The detection elements 321 detect incident X-rays by dividing the incident X-rays into a plurality of energy bins as shown in FIG. 2. In FIG. 2, X-rays detected while being divided into three energy bins, that is, an energy bin "T1 to T2", an energy bin "T2 to T3", and an energy bin "T3 and over" are shown as bin1, bin2, and bin3 respectively. Here, various combinations of X-rays may be calculated using the X-rays divided into the plurality of energy bins. For example, an X-ray intensity of bin1+bin2, or an X-ray intensity of bin2+bin3 may be calculated using X-ray intensities of bin1, X-ray intensities of bin2, and X-ray intensities of bin3.

The description returns to the explanation in FIG. 1. A circular opening 331 for disposing the table 102 on which the subject 101 is placed is provided at the center of the gantry 330. The diameter of the opening 331 is, for example, 700 mm. On the gantry 330, the X-ray source 310 and the X-ray detection device 320 are mounted, and further a rotation plate 332 for rotating the X-ray source 310 and the X-ray detection device 320 around the subject 101 is included. The table 102 is moved in the z direction to adjust the position of the subject 101 relative to the gantry 330.

The scanning control unit 340 includes: an X-ray control unit 341; a gantry control unit 342; a table control unit 343; and a detection device control unit 344. The X-ray control unit 341 controls a voltage and the like to be applied to the X-ray source 310. The gantry control unit 342 controls the rotation of the rotation plate 332, and rotates the rotation plate 332, for example, at 1.0 s/rotation. The detection device control unit 344 controls the detection of X-rays executed by the X-ray detection device 320, and makes the X-ray detection device 320 detect X-rays at 0.4 degrees/detection. The table control unit 343 controls the movement of the table 102.

The integral control unit 400 includes: a CPU (Central Processing Unit) 401; a memory 402; and a storage device 403, controls the scanning control unit 340, and performs various types of processing on projection data and the like obtained by the X-ray detection device 320. For example, the integral control unit 400 performs the processing of reconstructing tomographic images using the projection data obtained according to the scanning conditions set by the input device 210. The tomographic images may be reconstructed in units of the energy bins. In addition, the reconstructed tomographic images or the projection data used for the reconstruction may be displayed on the monitor 220, stored in the storage device 403, or treated in units of the energy bins. Furthermore, by scanning a combination of a plurality of base materials with their compositions and thicknesses known, material decomposition data used for creating material decomposition images can be obtained.

Figure 3:
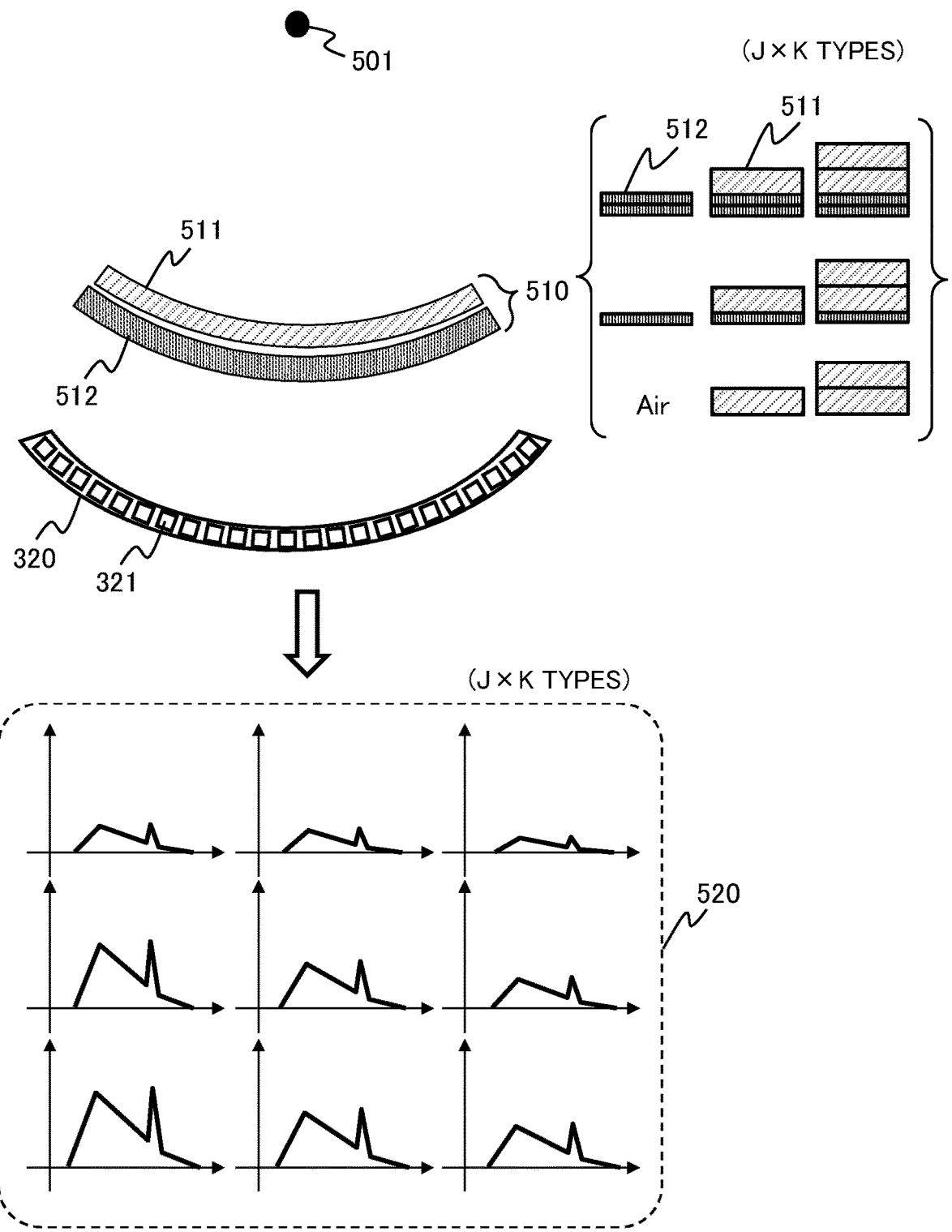
FIG. 3 is a diagram used for explaining material decomposition data.

Material decomposition data 520 used for creating material decomposition images will be explained with reference to FIG. 3. The material decomposition data 520 is composed of plural types of X-ray energy spectra obtained using calibration members 510 each composed of a plurality of base materials with known compositions and thicknesses. Each of the calibration members 510 is, for example, a combination of a first base material 511 and a second base material 512 each of which has a circular-arc shape centered on the X-ray focal point 501 and a uniform thickness. As the first base material 511, a material having a relatively small effective atomic number such as acrylic or polyethylene is used, and as the second base material 512, a material having a relatively large effective atomic number such as aluminum, calcium mixture, iodine mixture, or tin is used. Here, there are some cases where each of the first base material 511 and the second base material 512 has a plurality of different thicknesses. For example, if the first base material 511 has J types of thicknesses, and the second base material 512 has K types of thicknesses, J×K types of calibration members 510 are used, and an X-ray energy spectrum for each combination is obtained by each detection element 321. In FIG. 3, since J=3 and K=3, nine types of X-ray energy spectra are shown as material decomposition data 520. Here, the material decomposition data 520 is obtained in advance before scanning the subject 101.

The obtained material decomposition data 520 may be stored in the storage device 403, for example, as a material decomposition map 521 shown in FIG. 4. The material decomposition map 521 as illustrated in FIG. 4 shows a result in which X-rays transmitting through calibration members 510 composed of combinations of acrylic plates with their thicknesses 0 mm to 200 mm and aluminum plates with their thicknesses 0 mm to 8 mm are detected and divided into three energy bins. Here, the material decomposition map 521 is not limited to being displayed in a table as illustrated in FIG. 4, but also may be displayed in a graph, a mathematical formula, or the like.

A procedure for creating material decomposition images will be explained using the material decomposition data 520. The projection data of the subject 101 obtained at various scanning angles by the scanning unit 300 has an X-ray energy spectrum for each detection element 321. An X-ray energy spectrum that is the closest to an X-ray energy spectrum for each detection element 321 is searched for among the X-ray energy spectra of the material decomposition data 520, and a thickness combination of base materials corresponding to the searched-for X-ray energy spectrum is obtained. In other words, if the first base material 511 is acrylic and the second base material 512 is aluminum, the thickness of the acrylic and the thickness of the aluminum are obtained for each detection element 321 at various projection angles, and the projection data of the acrylic and the projection data of the aluminum are obtained. And, by reconstructing a tomographic image of each of the base materials using the projection image of each of the base materials, material decomposition images are created.

Figure 5:
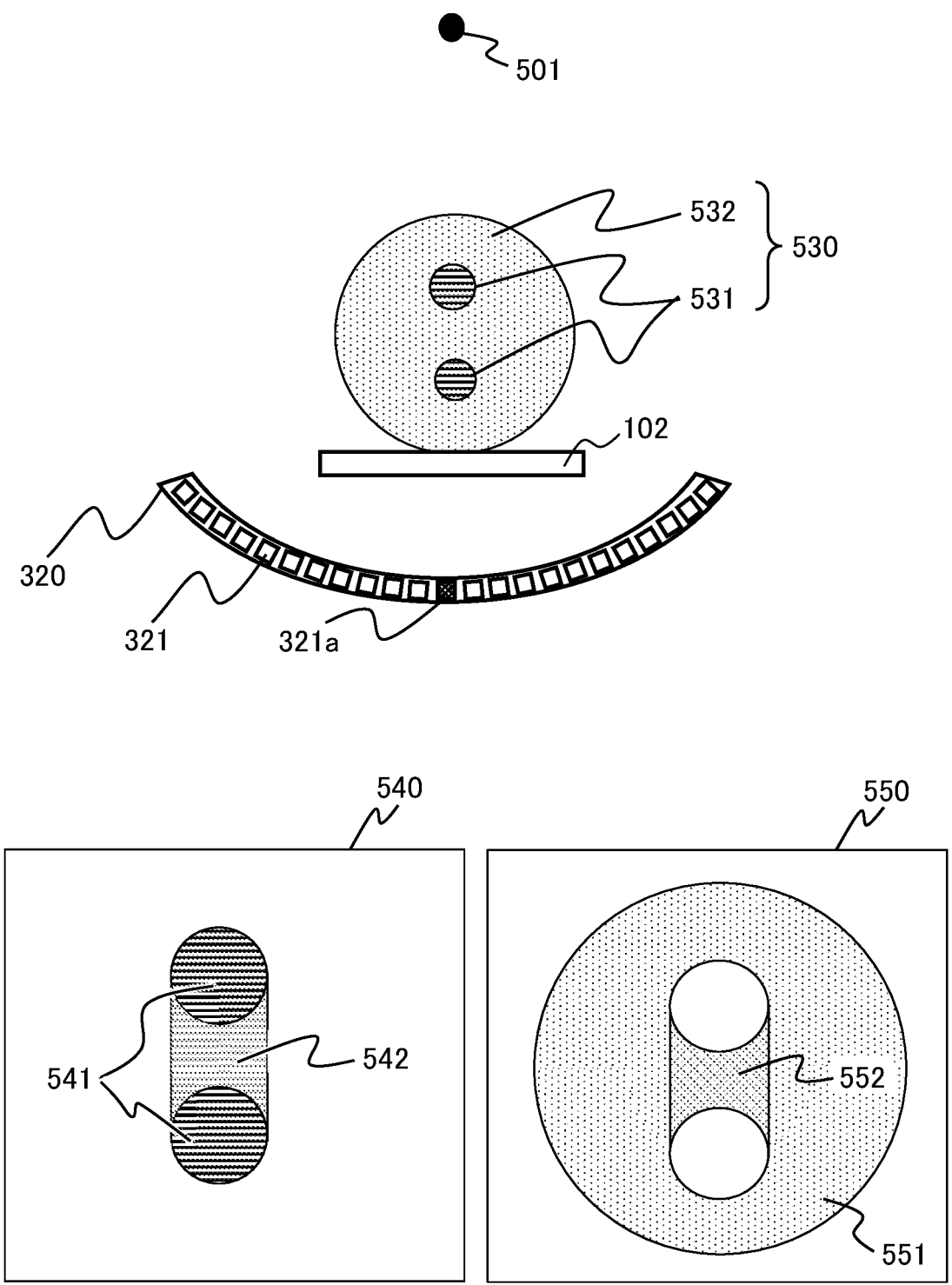
FIG. 5 is a diagram used for explaining the band artifacts of material decomposition images.

Band artifacts generated in material decomposition images will be explained with reference to FIG. 5. An aluminum image 540 and an acrylic image 550 are shown in FIG. 5 as material decomposition images created using the projection data of a phantom 530 that simulates a subject including sites having high X-ray absorption coefficients. The phantom 530 is an acrylic circular cylinder 532 including two aluminum rods 531. The two aluminum rods simulate the sites having high X-ray absorption coefficients. The acrylic circular cylinder 532 simulates a site other than the sites having high X-ray absorption coefficients.

An aluminum image 540, which is an image showing the distribution of aluminum, should display only two aluminum regions 541 corresponding to the two aluminum rods 531 in the phantom 530. However, a dark band 542, which is a band artifact having lower pixel values than its surrounding area, is generated between the two aluminum regions 541 corresponding to the sites having high X-ray absorption coefficients. In addition, an acrylic image 550, which is an image showing the distribution of acrylic, should have uniform pixel values in an acrylic region 551 corresponding to the acrylic circular cylinder 532. However, a bright band 552, which is a band artifact having higher pixel values than its surrounding area, is generated between regions corresponding to the two aluminum rods 531. A medical image including the dark band 542 or the bright band 552 brings about the degradation of diagnostic accuracy.

The dark band 542 and the bright band 552 are generated because the ratio of scattered rays included in X-rays incident on a detection element 321a located directly below the two aluminum rods 531 is larger than the ratio of scattered rays included in the material decomposition data 520. In other words, in FIG. 5, most of scattered rays generated by the acrylic circular cylinder 532 are incident on the detection element 321a, whereas in FIG. 3, scattered rays generated by the acrylic which is the first base material 511 are absorbed by the aluminum which is the second base material 512, so that scattered rays incident on the detection element 321a are relatively few. Therefore, even if a combination of the thickness of the two aluminum rods 531 and the thickness of the acrylic circular cylinder 532 is the same as a combination of the thickness of the first base material 511 and the thickness of the second base material 512, there is a difference between an X-ray energy spectrum in the case of the former combination and an X-ray spectrum in the case of the latter combination when detected by the detection element 321a, so that thicknesses obtained by material decomposition have errors. To put it concretely, since the X-ray spectrum obtained in FIG. 5 has a little larger X-ray intensities in the low energy side than the X-ray spectrum obtained in FIG. 3, the thicknesses of the two aluminum rods are obtained as thicknesses thinner than their actual thicknesses, and the thickness of the acrylic circular cylinder is obtained as a thickness thicker than its actual thickness, so that the dark band 542 and the bright band 552 occur due to the errors of the thicknesses. Here, a difference between the average energy of X-rays that have transmitted through the phantom 530 and the average energy of X-rays that have transmitted through the calibration member 510 is within a permissible range.

Although one of the dark band 542 and the bright band 552 can be dealt with by beam hardening correction, the other cannot be dealt with. Therefore, in the first embodiment, the band artifact of the other material decomposition image is corrected using a first correction amount that is a correction amount for correcting the band artifact of one material decomposition image and a second correction amount that is a correction amount calculated on the basis of the average energy of X-rays that have transmitted through the subject.

Figure 6:
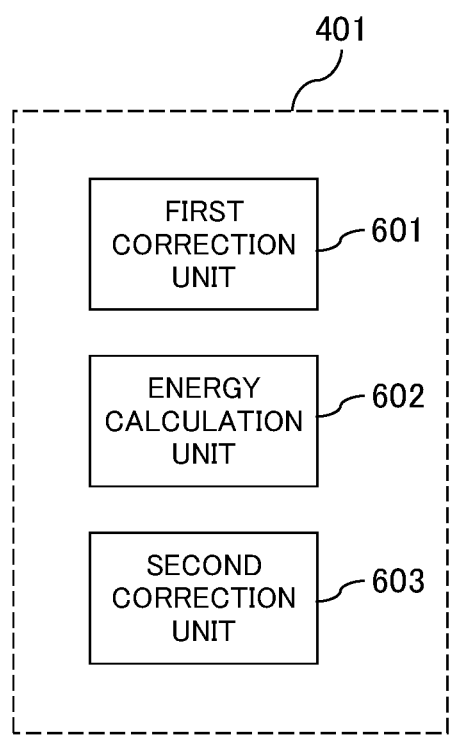
FIG. 6 is a diagram showing the functional blocks of a first embodiment.

The functional blocks of the first embodiment will be explained with reference to FIG. 6. Here, these functional blocks may be composed of dedicated hardware or software running on the CPU 401. In the following descriptions, it will be assumed that the functional blocks of the first embodiment are composed of software. In the first embodiment, a first correction unit 601, an energy calculation unit 602, and a second correction unit 603 are provided. Hereinafter, the abovementioned units will be explained.

The first correction unit 601 corrects the band artifact of a first material decomposition image, and at the same time, calculates the first correction amount that is a correction amount for correcting the band artifact of the first material decomposition image. A method for correcting the band artifact of the first material decomposition image may be an arbitrary method, and for example, may be a method disclosed in Japanese Unexamined Patent Application Publication No. 2009-50413. The first correction amount can be obtained by subtracting the material decomposition image with its not-yet-corrected band artifact from the material decomposition image with its already-corrected band artifact.

The energy calculation unit 602 calculates the average energy of X-rays that have transmitted through the subject 101. The average energy may be calculated on the basis of a virtual monochromatic image that is an image at a specific X-ray energy and created using a material decomposition image including a band artifact. In other words, a virtual monochromatic image having the smallest band artifact is extracted from among a plurality of virtual monochromatic images, and an X-ray energy corresponding to the extracted virtual monochromatic image is calculated as the average energy. Alternatively, the average energy may be calculated using the X-ray energy spectra of the projection data of the subject 101.

The second correction unit 603 calculates the second correction amount on the basis of the first correction amount and the average energy, and at the same time, corrects the band artifact of the other material decomposition image using the second correction amount. The second correction amount COR2 is calculated using, for example, the following expression.

$$COR2 = \mu1(E) \cdot \rho1 \cdot COR1 / (\mu2(E) \cdot \rho2) \quad \text{(Expression 1)},$$

where $\mu1(E)$ is the X-ray attenuation coefficient of a first material at an X-ray energy E; $\rho1$ is the density of the first material; COR1 is the first correction amount; $\mu2(E)$ is the X-ray attenuation coefficient of a second material at the X-ray energy E; $\rho2$ is the density of the second material; and the average energy is used as E.

An example of the processing flow of the first embodiment will be explained step by step with reference to FIG. 7.

(S701)

The integral control unit 400 obtains the projection data of the subject 101 by controlling the scanning control unit 340.

(S702)

The integral control unit 400 performs material decomposition on the projection data obtained in S701, and obtains the projection data of the first material and the projection data of the second material. For the material decomposition, for example, the material decomposition data 520 obtained in advance is used.

(S703)

The integral control unit 400 creates a first material decomposition image and a second material decomposition image by reconstructing the projection data of the first material and the projection data of the second material that are obtained in S702 respectively.

(S704)

The integral control unit 400 creates a plurality of virtual monochromatic images using the first material decomposition image and the second material decomposition image obtained in S703. The pixel value V of a virtual monochromatic image at the X-ray energy E is calculated using, for example, the following expression.

$$V = \mu1(E) \cdot \rho1 \cdot M1 + \mu2(E) \cdot \rho2 \cdot M2 \quad \text{(Expression 2)},$$

where μ1(E) is the X-ray attenuation coefficient of the first material at the X-ray energy E; ρ1 is the density of the first material; M1 is the pixel value of the first material decomposition image; μ2(E) is the X-ray attenuation coefficient of the second material at the X-ray energy E; ρ2 is the density of the second material; and M2 is the pixel value of the second material decomposition image.

(S705)

The integral control unit 400 judges whether or not there are band artifacts in the first material decomposition image, in the second material decomposition image obtained in S703, or in the virtual monochromatic images created in S704. If there are band artifacts, the flow proceeds to processing in S706, and if not, the flow proceeds to processing in S708. Whether there are band artifacts or not may be judged by a judgment device created in advance by machine learning, or may be judged by an operator.

(S706)

The integral control unit 400 corrects the band artifacts of the material decomposition images.

An example of the flow of the correction processing of the material decomposition images performed in S706 will be explained step by step with reference to FIG. 8.

(S801)

The first correction unit 601 corrects the band artifact of one material decomposition image, for example, the dark band 542 of the aluminum image 540. The band artifact is corrected by, for example, the beam hardening correction.

(S802)

The first correction unit 601 calculates the first correction amount that is a correction amount for correcting the band artifact of the one material decomposition image. The first correction amount can be calculated by subtracting the not-yet-corrected aluminum image 540 from the already-corrected aluminum image obtained in S801.

(S803)

The energy calculation unit 602 calculates the average energy of X-rays that transmit the subject 101. For example, a virtual monochromatic image having the smallest band artifact is extracted from among the plurality of virtual monochromatic images created in S704, and an X-ray energy corresponding to the extracted virtual monochromatic image is calculated as the average energy. Alternatively, the average energy may be calculated using the X-ray energy spectra of the projection data obtained in S701.

(S804)

The second correction unit 603 calculates the second correction amount on the basis of the first correction amount calculated in S802 and the average energy calculated in S803. The second correction amount is calculated by, for example, Expression 1.

(S805)

The second correction unit 603 corrects the band artifact of the other material decomposition image, for example, the bright band 552 of the acrylic image 550 using the second correction amount calculated in S804. In other words, by adding the second correction amount to the other material decomposition image, for example, to the acrylic image 550, the bright band 552 that is the band artifact of the other material decomposition image is corrected.

Figure 7:
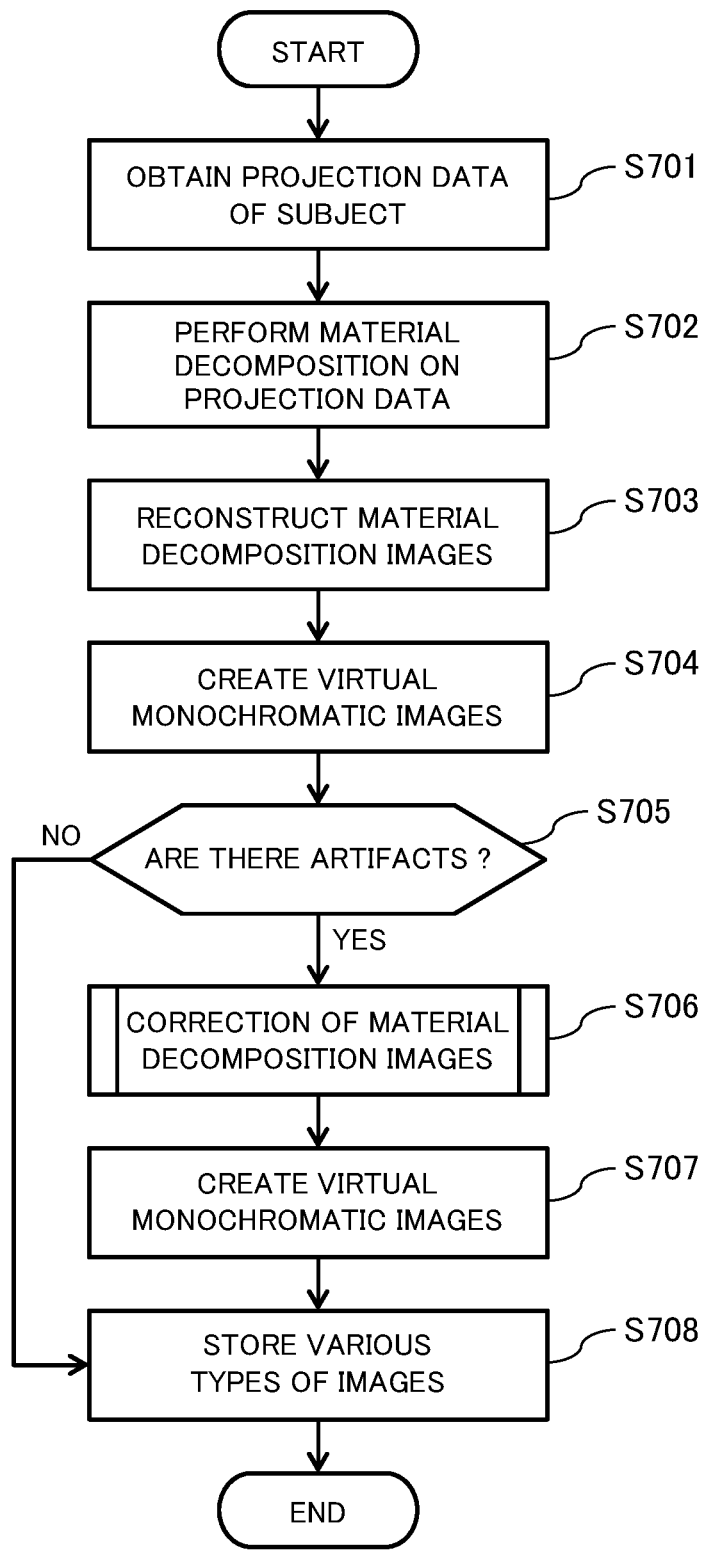
FIG. 7 is a diagram showing an example of the processing flow of the first embodiment.
Figure 8:
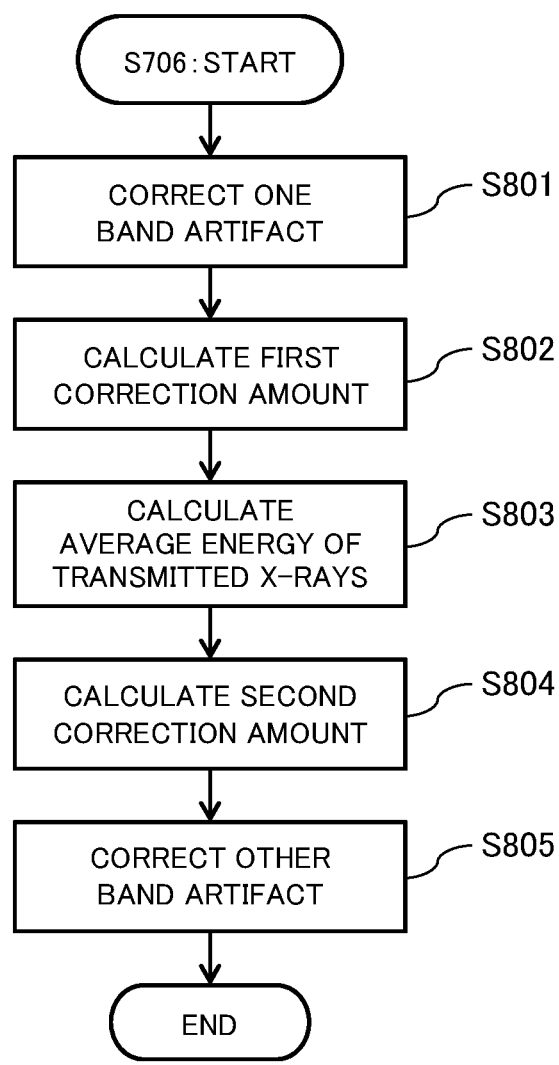
FIG. 8 is a diagram showing an example of the flow of the correction processing of material decomposition images.

According to the flow of the correction processing illustrated in FIG. 8, the band artifact of the one material decomposition image is corrected, and the band artifact of the other material decomposition image is corrected as well. The description returns to the explanation of FIG. 7.

(S707)

The integral control unit 400 creates virtual monochromatic images using the first material decomposition image and the second material decomposition image corrected in S706. The pixel value of a virtual monochromatic image is calculated using, for example, Expression 2.

The integral control unit 400 stores the first material decomposition image and the second material decomposition image corrected in S706, or the virtual monochromatic images created in S704 and S707 in the storage device 403. The material decomposition images and the virtual monochromatic images stored in the storage device 403 are displayed on the monitor 220 as needed and used for diagnosis.

According to the processing flow illustrated in FIG. 7, the material decomposition images with their band artifacts corrected and the virtual monochromatic images are created, so that the accuracy of diagnosis can be improved.

The embodiment of the present invention has been described. Here, it should be noted that the present invention is not limited to the above-described embodiment, and can be embodied by modifying the components without departing from the gist of the present invention. Furthermore, a plurality of components disclosed in the above embodiment may be appropriately combined. In addition, some components may be deleted from all the components shown in the above embodiment.

REFERENCE SIGNS LIST

100: PCCT apparatus, 101: subject, 102: table, 201: input/output unit, 210: input device, 220: monitor, 300: scanning unit, 310: X-ray source, 311: collimator, 320: X-ray detection device, 321: detection element, 330: gantry, 331: opening, 332: rotation plate, 340: scanning control unit, 341: X-ray control unit, 342: gantry control unit, 343: table control unit, 344: detection device control unit, 400: integral control unit, 401: CPU, 402: memory, 403: storage device, 501: X-ray focal point, 510: calibration member, 511: first base material, 512: second base material, 520: material decomposition data, 521: material decomposition map, 531: aluminum rod, 532: acrylic circular cylinder, 540: aluminum image, 541: aluminum region, 542: dark band, 550: acrylic image, 551: acrylic region, 552: bright band, 601: first correction unit, 602: energy calculation unit, 603: second correction unit

What is claimed is:

1. A PCCT apparatus that obtains projection data divided into a plurality of energy bins by irradiating a subject with X-rays, the PCCT apparatus comprising:
   a first correction unit that corrects a band artifact of a first material decomposition image among a plurality of material decomposition images created on the basis of the projection data, and at the same time, calculates a first correction amount that is a correction amount for the band artifact;
   an energy calculation unit that calculates an average energy of X-rays that transmit the subject; and
   a second correction unit that corrects the band artifact of a second material decomposition image using a second correction amount that is a correction amount calculated on the basis of the first correction amount and the average energy.

2. The PCCT apparatus according to claim 1, wherein the energy calculation unit calculates the average energy on the basis of a plurality of virtual monochromatic images created using the first material decomposition image and the second material decomposition image.

3. The PCCT apparatus according to claim 2, wherein the energy calculation unit extracts a virtual monochromatic image having the smallest band artifact from among the plurality of virtual monochromatic images, and sets an X-ray energy corresponding to the extracted virtual monochromatic image as the average energy.

4. The PCCT apparatus according to claim 1, wherein the energy calculation unit calculates the average energy using the X-ray energy spectra of the projection data.

5. The PCCT apparatus according to claim 1, wherein the second correction unit calculates a second correction amount COR2 using $COR2 = \mu1(E) \cdot \rho1 \cdot COR1 / (\mu2(E) \cdot \rho2)$ when an X-ray attenuation coefficient of a first material at an average energy E is $\mu1(E)$, a density of the first material is $\rho1$, an X-ray attenuation coefficient of a second material at the average energy E is $\mu2(E)$, a density of the second material is $\rho2$, and a first correction amount is COR1.

6. The PCCT apparatus according to claim 1, wherein the first correction unit corrects the band artifact of the first material decomposition image using beam hardening correction.

\* \* \* \* \*